United States Patent
Streshinsky et al.

(10) Patent No.: US 10,429,313 B2
(45) Date of Patent: Oct. 1, 2019

(54) METHODS, TEST STRUCTURES, AND TEST SYSTEMS FOR DETERMINING A SURFACE CHARACTERISTIC OF A CHIP FACET

(71) Applicant: Elenion Technologies, LLC, New York, NY (US)

(72) Inventors: Matthew Akio Streshinsky, New York, NY (US); Ari Novack, New York, NY (US); Michael J. Hochberg, New York, NY (US)

(73) Assignee: Elenion Technologies, LLC, New York, NY (US)

(*) Notice: Subject to any disclaimer, the term of this patent is extended or adjusted under 35 U.S.C. 154(b) by 222 days.

(21) Appl. No.: 15/427,185

(22) Filed: Feb. 8, 2017

(65) Prior Publication Data

US 2018/0224501 A1 Aug. 9, 2018

(51) Int. Cl.
| | |
|---|---|
| *G01R 31/311* | (2006.01) |
| *G01N 21/88* | (2006.01) |
| *G01B 11/30* | (2006.01) |
| *H01L 21/66* | (2006.01) |
| *G01R 31/308* | (2006.01) |

(52) U.S. Cl.
CPC ......... *G01N 21/8806* (2013.01); *G01B 11/30* (2013.01); *G01R 31/311* (2013.01); *H01L 22/12* (2013.01); *H01L 22/30* (2013.01); *G01R 31/308* (2013.01)

(58) Field of Classification Search
CPC .... G01R 31/00; G01R 31/26; G01R 31/2601; G01R 31/2642; G01R 31/2648; G01R 31/265; G01R 31/2808; G01R 31/2831; G01R 31/2851; G01R 31/302; G01R 31/303; G01R 31/3012; G01R 31/307; G01R 31/308; G01R 31/311; G01R 31/31702; G01R 31/318511; G01R 1/0491; G01R 1/07; G01R 1/071; G01N 21/00; G01N 21/84; G01N 21/88; G01N 21/8806; G01B 11/00; G01B 11/30; H01L 22/00; H01L 22/10; H01L 22/12; H01L 22/30
USPC ......... 324/500, 537, 750.16, 750.23, 754.01, 324/754.03, 754.06, 754.21, 754.23, 324/762.01, 762.02, 762.03, 762.05, 324/76.11, 76.77, 84, 95
See application file for complete search history.

(56) References Cited

U.S. PATENT DOCUMENTS

| | | | | |
|---|---|---|---|---|
| 4,583,861 | A * | 4/1986 | Yamaji | G01N 21/4738 356/446 |
| 5,239,183 | A * | 8/1993 | Kouno | G01B 11/026 250/559.31 |
| 6,356,399 | B1 * | 3/2002 | Haga | G01B 11/255 356/237.2 |

(Continued)

*Primary Examiner* — Hoai-An D. Nguyen
(74) *Attorney, Agent, or Firm* — Stratford Managers Corporation

(57) ABSTRACT

A test system for determining a surface characteristic of a chip facet includes an on-chip waveguide, a detector, and a processor. The on-chip waveguide is configured to direct test light towards the facet, where a portion of the test light is reflected and a portion of the test light is transmitted. The detector is configured to measure an amount of the reflected portion or the transmitted portion, and the processor is configured to determine a surface characteristic of the facet, such as a facet angle, a facet curvature, and/or a facet roughness, on the basis of the measured amount.

16 Claims, 21 Drawing Sheets

(56) References Cited

U.S. PATENT DOCUMENTS

| | | | | |
|---|---|---|---|---|
| 7,999,941 | B2* | 8/2011 | Matsushita | G01J 3/02 |
| | | | | 356/445 |
| 10,161,884 | B2* | 12/2018 | Ullrich | G01B 5/003 |
| 2003/0025091 | A1* | 2/2003 | Kaneko | G01N 21/55 |
| | | | | 250/559.19 |
| 2008/0243412 | A1* | 10/2008 | Horie | G01N 21/9501 |
| | | | | 702/82 |
| 2012/0050739 | A1* | 3/2012 | Hayano | G01B 11/24 |
| | | | | 356/369 |

* cited by examiner

METHODS, TEST STRUCTURES, AND TEST SYSTEMS FOR DETERMINING A SURFACE CHARACTERISTIC OF A CHIP FACET

FIELD OF THE INVENTION

The present invention relates to methods, test structures, and test systems for determining a surface characteristic of a chip facet. More particularly, the present invention relates to methods, test structures, and test systems for determining a surface characteristic of a facet of a photonic chip including a waveguide.

BACKGROUND OF THE INVENTION

In devices and systems incorporating photonic chips, it is often necessary to couple light from an on-chip waveguide into an off-chip optical fiber. With reference to FIG. 1, in a conventional edge coupling arrangement, a photonic chip 110 includes a waveguide 120, such as an edge coupler, that directs light towards a facet 130 of the photonic chip 110. The light is coupled out of the facet 130 into an off-chip optical fiber 140. Typically, owing to fabrication process limitations, the facet 130 is not perfectly perpendicular to the propagation path of the light and the plane of the photonic chip 110, which can reduce coupling efficiency. Accordingly, it is desirable to determine the facet angle θ, defined relative to the plane of the photonic chip 110 in FIG. 1.

Conventionally, scanning electron microscopic (SEM) techniques are used to determine the facet angle. In one technique, the facet angle is determined from top-view or perspective-view SEM images of chips on a wafer. Unfortunately, the accuracy and throughput of this technique may be inadequate, and the number of measurement sites that can be accommodated by the technique may be limited. In another technique, the facet angle is determined from cross-sectional SEM images of chips on a wafer. Although this technique provides a higher accuracy, the technique often requires additional and/or destructive processing steps.

Accordingly, there is a need for new methods, test structures, and test systems for determining the facet angle and other surface characteristics of a chip facet, particularly at the wafer scale.

SUMMARY OF THE INVENTION

Accordingly, an aspect of the present invention relates to a test system for determining a surface characteristic of a chip facet, the test system comprising: a chip having a facet, the chip including a waveguide configured to direct test light towards the facet; a detector configured to measure an amount of a portion of the test light reflected by the facet or a portion of the test light transmitted by the facet; and a processor configured to determine a surface characteristic of the facet on the basis of the measured amount.

Another aspect of the present invention relates to a method of determining a surface characteristic of a chip facet, the method comprising: providing a chip having a facet, the chip including a waveguide; directing test light towards the facet via the waveguide; measuring an amount of a portion of the test light reflected by the facet or a portion of the test light transmitted by the facet; and determining a surface characteristic of the facet on the basis of the measured amount.

BRIEF DESCRIPTION OF THE DRAWINGS

Numerous exemplary embodiments of the present invention will now be described in greater detail with reference to the accompanying drawings wherein.

DETAILED DESCRIPTION OF THE INVENTION

Figure 1:
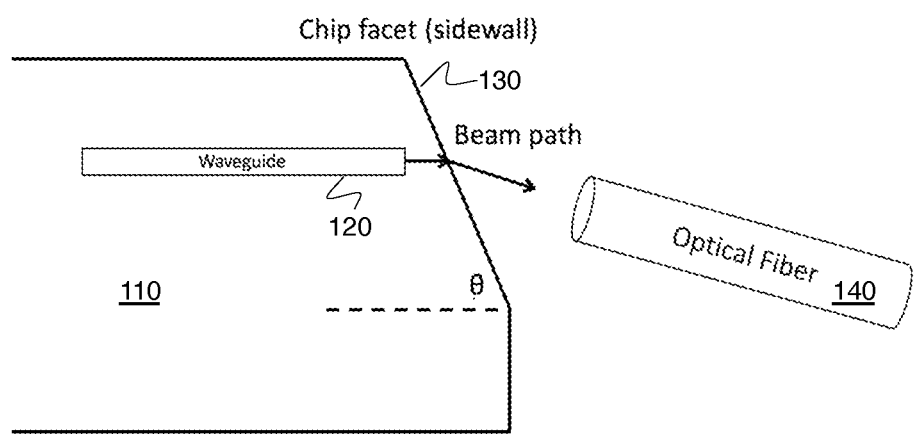
FIG. 1 is a schematic illustration of a cross-sectional side view of a conventional edge-coupling arrangement.

The present invention provides methods, test structures, and test systems for determining a surface characteristic of a chip facet, typically a facet of a photonic chip. Advantageously, the methods, test structure, and test systems may be used to determine the surface characteristic of the chip facet at the wafer scale, i.e., while the photonic chip is on a wafer, prior to dicing or packaging. The methods, test structures, and test systems may be implemented with any suitable type of integrated photonics platform, for example, a silicon-on-insulator (SOI) platform, e.g., with silicon and/or silicon nitride waveguides, a silica-on-silicon platform, or a III-V material platform.

In general, the photonic chip includes a facet and at least one waveguide. The facet is typically an edge facet disposed at an edge of the photonic chip, and a top edge of the facet typically forms the chip edge. The facet is typically formed as a sidewall of a trench in the wafer, e.g., by etching. The facet may be substantially perpendicular to a plane of the photonic chip, and typically to a plane of the wafer, or may be inclined relative to the chip plane. The facet may be coated with an antireflective coating.

The waveguide may be any suitable type of waveguide, for example, a ridge waveguide, e.g., a narrow single-mode ridge waveguide or a wide multi-mode ridge waveguide, a strip waveguide, or a slot waveguide. The waveguide is typically formed in the photonic chip, i.e., formed on or in a substrate or layer of the photonic chip. Accordingly, the waveguide is typically disposed substantially parallel to the chip plane. In some embodiments, the waveguide or a segment thereof is disposed substantially perpendicular to the top edge of the facet, and typically to the chip edge. In other embodiments, the waveguide or a segment thereof is disposed at an oblique angle to the top edge of the facet. In yet other embodiments, the waveguide or a segment thereof is disposed substantially parallel to the top edge of the facet.

Several exemplary embodiments of test structures that can be used in methods and test systems for determining a surface characteristic of a chip facet are described hereafter. It should be understood that individual elements of any of the exemplary embodiments may be combined as appropriate to arrive at further embodiments.

In the exemplary embodiments of FIGS. 2-13, the test structure comprises a chip 210, typically a photonic chip, that includes a first waveguide 220 configured to direct test light towards the facet 230 in a direction substantially perpendicular to a top edge of a facet 230 of the photonic chip 210. At least an output segment of the first waveguide 220 is disposed substantially perpendicular to the top edge of the facet 230. When the test light is incident on the facet 230, a portion of the test light is reflected by the facet 230, and a portion of the test light is transmitted by the facet 230.

The test structure may be included in a test system that also includes a light source, a detector, and/or a processor. The light source, e.g., a laser or a broadband light source, is configured to provide the test light. The detector, e.g., a photodetector, is configured to measure an amount, e.g., an optical power, of the reflected portion of the test light or the transmitted portion of the test light. Typically, the detector detects the reflected portion of the test light or the transmitted portion of the test light and provides an output signal representative of the amount of the reflected portion of the test light or the transmitted portion of the test light to the processor. The processor, e.g., a general-purpose processor or a special-purpose processor, is configured, e.g., programmed with instructions, to determine a surface characteristic of the facet 230, such as a facet angle, a facet curvature, and/or a facet roughness, on the basis of the measured amount. Typically, the surface characteristic is determined by using a empirical model, such as a calibration curve, relating the measured amount to the surface characteristic.

Figure 2:
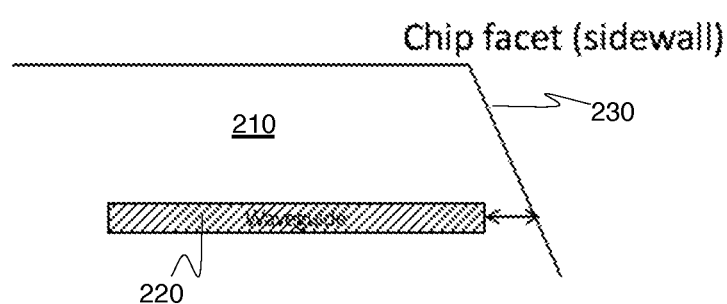
FIG. 2 is a schematic illustration of a cross-sectional side view of a test structure.

In the embodiment of FIG. 2, the first waveguide 220 is configured to receive the reflected portion of the test light from the facet 230, and the detector is configured to measure the amount of the reflected portion of the test light. An optical circulator may be used as both an input port configured to couple the test light from an off-chip light source into the first waveguide 220 and as an output port configured to couple the reflected portion of the test light to an off-chip detector. Alternatively, an off-chip reflectometer may be used as a detector.

Figure 3:
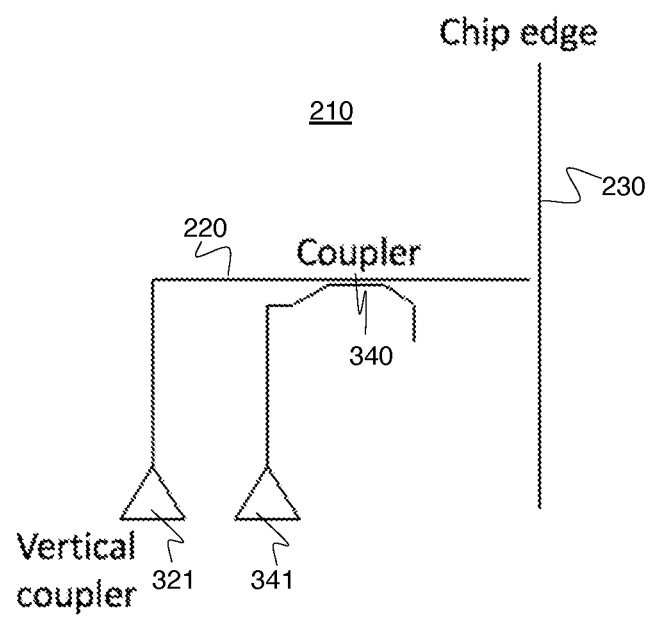
FIG. 3 is a schematic illustration of a top view of a test structure.

In the embodiment of FIG. 3, the photonic chip 210 further includes a first vertical coupler 321, e.g., a grating coupler, as an input port, a second waveguide 340, and a second vertical coupler 341, e.g., a grating coupler, as an output port. The first vertical coupler 321 is configured to couple the test light from an off-chip light source into the first waveguide 220. The second waveguide 340 is coupled to the first waveguide 220 to receive the reflected portion of the test light from the first waveguide 220. The first waveguide 220 and the second waveguide 340 may be coupled by a directional coupler, as shown in FIG. 3, or a multimode interference (MMI) coupler, e.g., a 2×1 MMI coupler or a 2×2 MMI coupler. The second vertical coupler 341 is configured to couple the reflected portion of the test light from the second waveguide 340 to an off-chip detector configured to measure the amount of the reflected portion of the test light.

Figure 4:
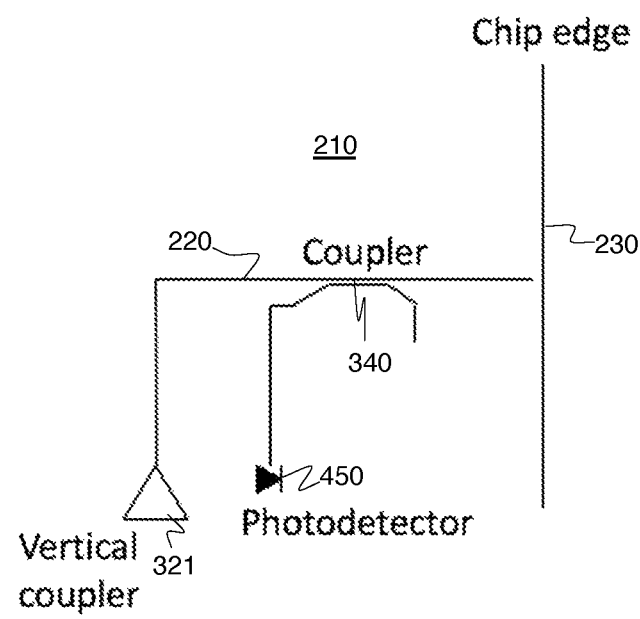
FIG. 4 is a schematic illustration of a top view of a test structure.

The embodiment of FIG. 4 is similar to the embodiment of FIG. 3, but the photonic chip 210 includes an on-chip detector 450, e.g., a photodetector, configured to measure the amount of the reflected portion of the test light, in place of the second vertical coupler 341.

Figure 5:
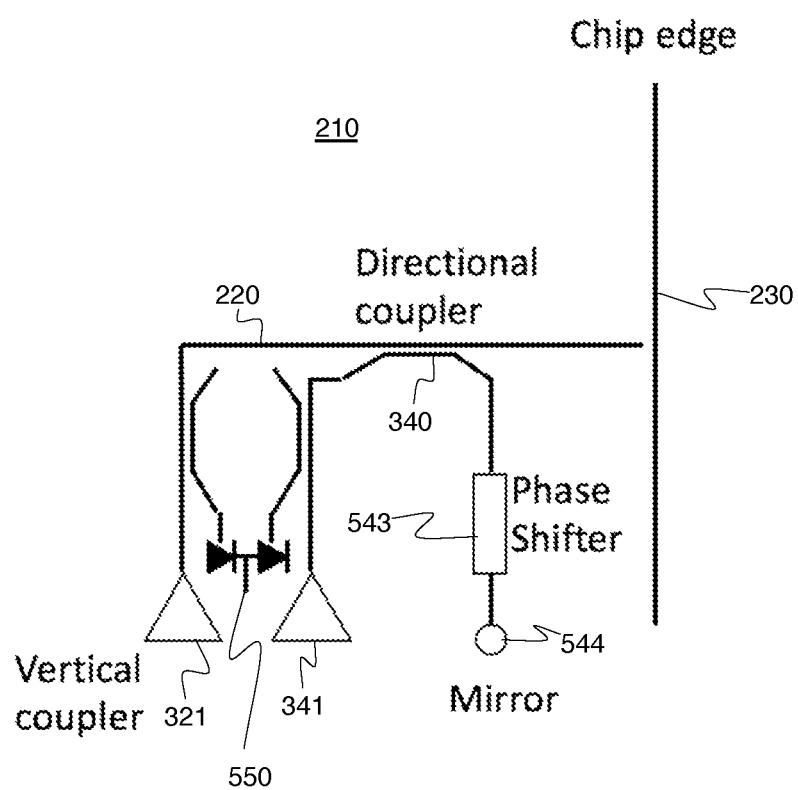
FIG. 5 is a schematic illustration of a top view of a test structure.

The embodiment of FIG. 5 is similar to the embodiment of FIG. 3, but the photonic chip 210 further includes a phase shifter 543 and a mirror 544, which together with the first waveguide 220 and the second waveguide 340 are included in an on-chip Michelson interferometer. The first waveguide 220 forms a test arm of the Michelson interferometer and is configured to direct test light towards the facet 230. The second waveguide 340 forms a reference arm of the Michelson interferometer and is configured to direct reference light towards the mirror 544. In some embodiments, the reference arm has an adjustable optical path length. For example, the optical path length may be thermally adjustable or may be adjustable by adjusting a charge-carrier concentration in the reference arm. The phase shifter 543 is configured to phase shift the reference light. The photonic chip 210 also includes an on-chip balanced photodetector 550 configured to receive the reflected portion of the test light from the test arm and the reflected reference light from the reference arm, and to measure the amount of the reflected portion of the test light as an interference pattern. Other similar embodiments may use an off-chip balanced photodetector and/or an off-chip Michelson interferometer.

Advantageously, the use of a Michelson interferometer may enhance the signal of the reflected portion of the test light, providing a larger dynamic range and improved measurement sensitivity. To illustrate how the signal of the reflected portion of the test light may be enhanced, a Michelson interferometer including a 2×2 MMI coupler may be considered. If two signals with respective optical powers of $P_1$ and $P_2$ enter the two input ports of the 2×2 MMI coupler, the output optical power $P_{out}$ from each of the output ports of the 2×2 MMI coupler will be $\frac{1}{2}[P_1+P_2+2\sqrt{P_1 P_2} \cos(\Delta\phi)]$, where $\Delta\phi$ is the relative phase shift between the electric fields of the two signals. If the output optical power from each of the two paths is input to a balanced photodetector 550, then the output photocurrent from the balanced photodetector 550 will be proportional to $2\sqrt{P_1 P_2} \cos(\Delta\phi)$. If we assume that $P_1$ is the optical power of the portion of the test light reflected by the facet 230, and that $P_2$ is the optical power of reference light reflected from a mirror 544 with a reflectivity of 100%, then $P_1$ is likely to be smaller than $P_2$. If the relative phase shift between the two signals is modulated through $2\pi$ by the phase shifter 543, then the interference signal at the balanced photodetector 550 will have a power greater than $P_1$ alone. In this way, the amount of the reflected portion of the test light can be more easily measured, even when the amount is relatively small.

Figure 6:
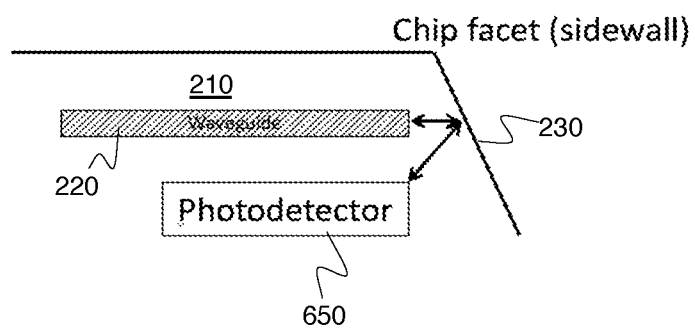
FIG. 6 is a schematic illustration of a cross-sectional side view of a test structure.

In the embodiment of FIG. 6, the photonic chip 210 further includes an integrated photodetector 650, e.g., a large-area photodetector. The integrated photodetector 650 is disposed near the facet 230 at a different height from the first waveguide 220, and is configured to receive the reflected portion of the test light from the facet 230 and to measure an amount of the reflected portion of the test light. The integrated photodetector 650 may be disposed above or below, as shown in FIG. 6, the first waveguide 220. Advantageously, the use of an integrated photodetector 650 may allow a larger portion of the test light reflected by the facet 230 to be detected and measured, since there is no need to couple the reflected portion of the test light into a waveguide.

Figure 7:
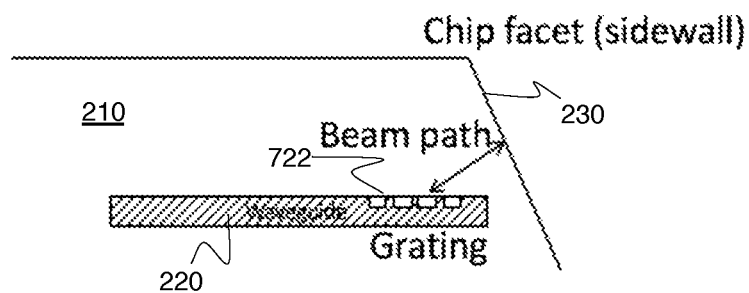
FIG. 7 is a schematic illustration of a cross-sectional side view of a test structure.
Figure 8:
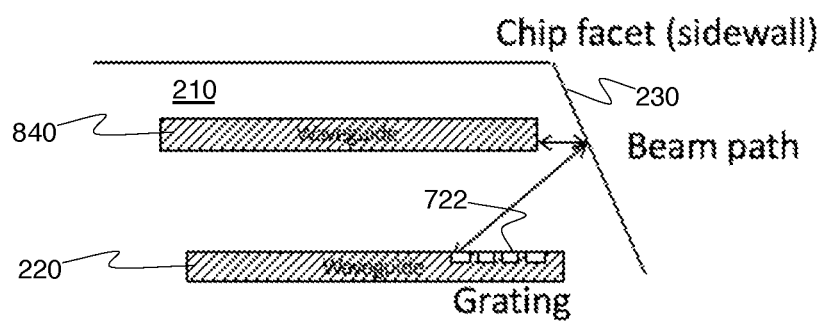
FIG. 8 is a schematic illustration of a cross-sectional side view of a test structure.
Figure 9:
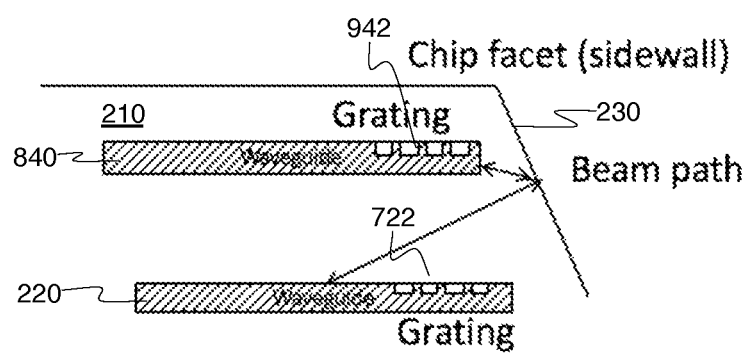
FIG. 9 is a schematic illustration of a cross-sectional side view of a test structure.

In the embodiments of FIGS. 7 to 9, the first waveguide 220 includes a grating structure 722 configured to diffract the test light exiting the first waveguide 220. The grating structure 722 is typically formed, e.g., etched, in the first waveguide 220 near an output end thereof.

In the embodiment of FIG. 7, the facet 230 is intentionally inclined, and the grating structure 722 is configured to diffract the test light such that the test light is directed towards the facet 230 in a direction substantially perpendicular to the inclined facet 230. Typically, the grating structure 722 is configured to diffract the test light upwards by a diffraction angle that is substantially equal in magnitude to 90° minus a desired facet angle defined relative to the chip plane. Such an embodiment may provide more efficient coupling of the reflected portion of the test light into first waveguide 220.

In the embodiments of FIGS. 8 and 9, the photonic chip 210 further includes a second waveguide 840 disposed at a different height from the first waveguide 220 and configured to receive the reflected portion of the test light from the facet 230, and the detector is configured to measure an amount of the reflected portion of the test light. The second waveguide 840 may be disposed above, as shown in FIGS. 8 and 9, or below the first waveguide 220, and may, as shown in FIG. 9, or may not, as shown in FIG. 8, include a grating structure 942. Typically, the first waveguide 220 and the second waveguide 840 are incorporated at different layers in the photonic chip 210, e.g., at different dielectric layers in an SOI chip. Since the facet angle may cause the reflected portion of the test light to be reflected at an angle, the additional second waveguide 840 at a different height from the first waveguide 220 may increase the sensitivity of the measurement. In other similar embodiments, the second waveguide 840 may be connected to optical circuits similar to those shown in FIGS. 3 to 5.

In some embodiments, the facet 230 includes a lithographically defined feature, e.g., a lens, near the first waveguide 220, that is configured to facilitate reflection of the reflected portion of the test light or to facilitate transmission of the transmitted portion of the test light. In a non-illustrated embodiment, the lithographically defined feature is configured to facilitate coupling of the reflected portion of the test light into the first waveguide 220, and the detector is configured to measure an amount of the reflected portion of the test light.

Figure 10A:
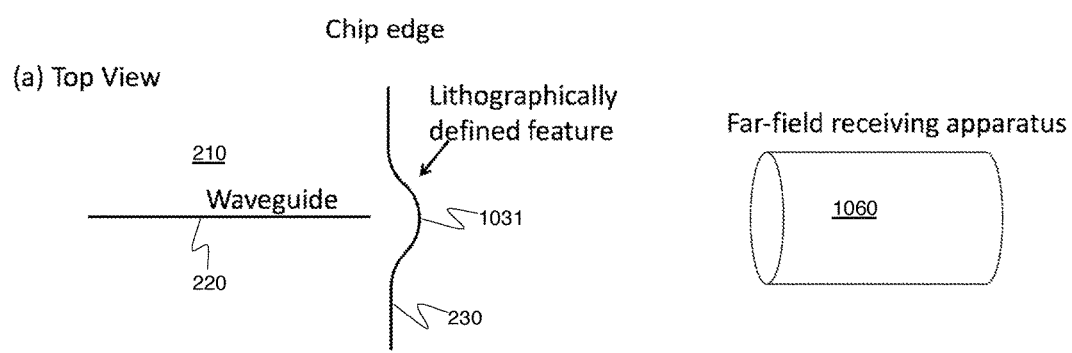
FIG. 10A is a schematic illustration of a top view of a test structure.
Figure 10B:
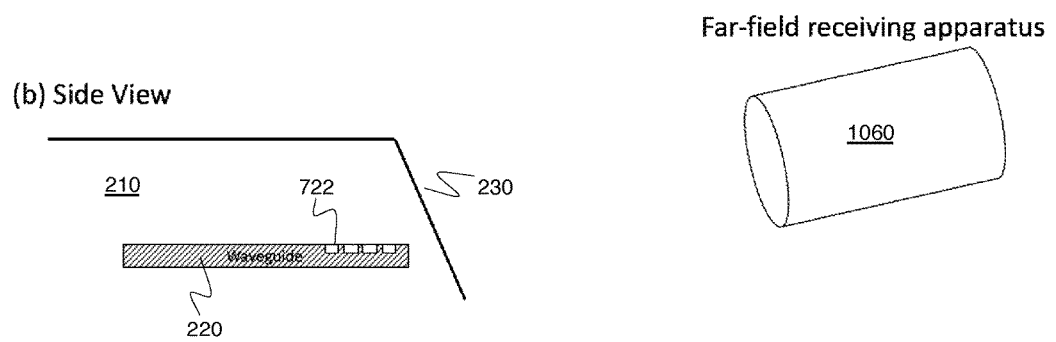
FIG. 10B is a schematic illustration of a cross-sectional side view of the test structure of FIG. 10A.

In the embodiment of FIG. 10, the lithographically defined feature 1031 is configured to facilitate far-field imaging of the transmitted portion of the test light. The first waveguide 220 may or may not include the grating structure 722 shown in FIG. 10B. A far-field receiving element 1060, e.g., an optical fiber or a spatial imager, is configured to receive the transmitted portion of the test light from the facet 230. In some instances, the detector is configured to receive the transmitted portion of the test light from the receiving element 1060 and to measure an amount of the transmitted portion of the test light. In other instances, the lithographically defined feature 1031 may be designed so that changes in a surface characteristic of the facet 230, e.g., facet angle, produce different far-field patterns.

Figure 11:
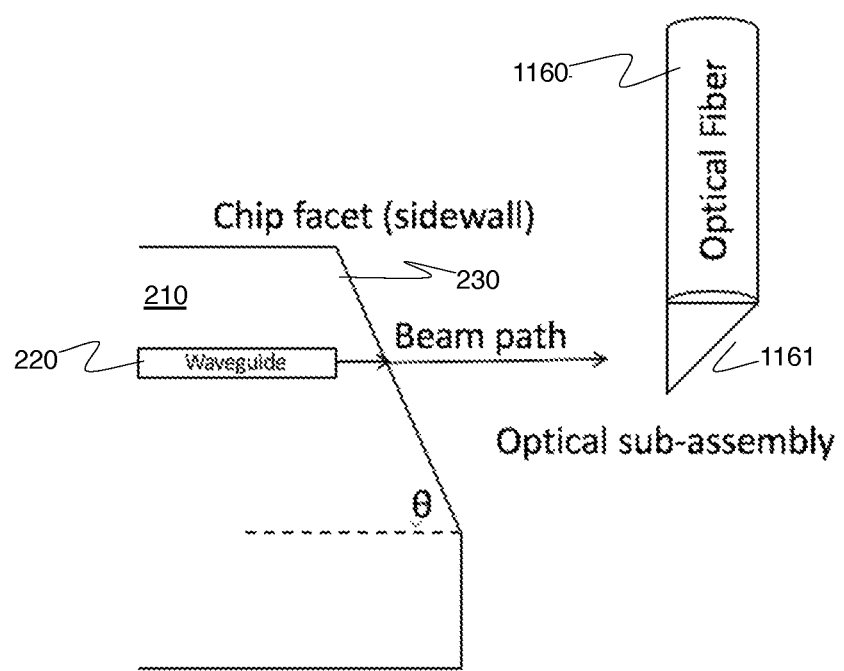
FIG. 11 is a schematic illustration of a cross-sectional side view of a test structure.
Figure 12:
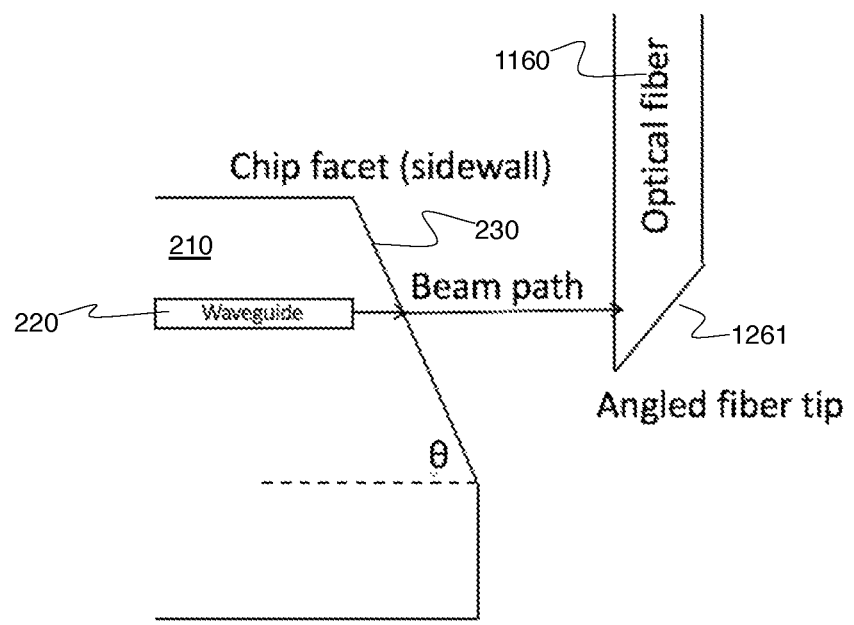
FIG. 12 is a schematic illustration of a cross-sectional side view of a test structure.
Figure 13:
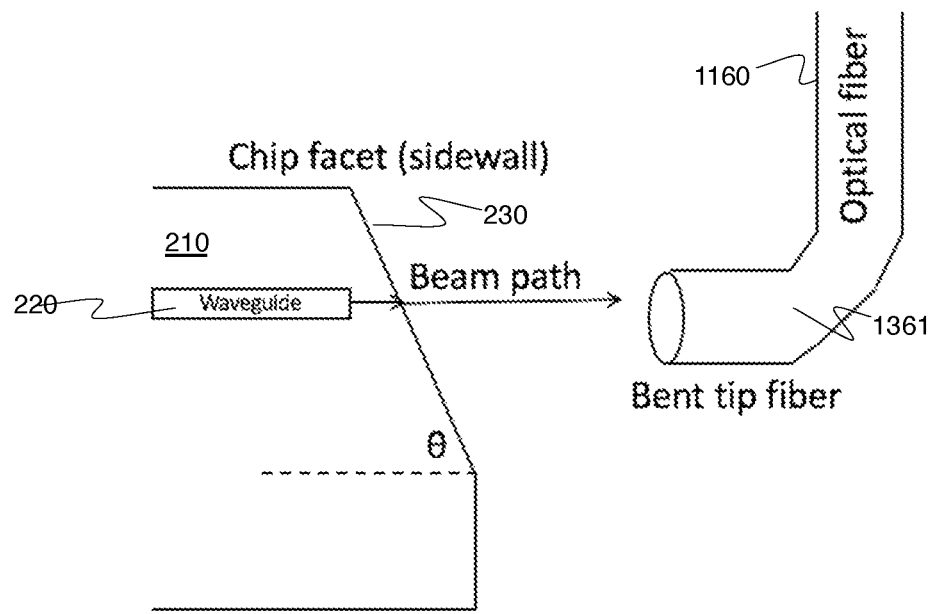
FIG. 13 is a schematic illustration of a cross-sectional side view of a test structure.

In the embodiments of FIGS. 11-13, an optical fiber 1160 is configured to receive the transmitted portion of the test light from the facet 230 via an input end of the optical fiber 1160, and the detector is configured to receive the transmitted portion of the test light from the optical fiber 1160 and to measure an amount of the transmitted portion of the test light. During testing, the optical fiber 1160 is disposed substantially perpendicular to the chip plane, i.e., substantially vertically, such that the input end thereof is disposed near the first waveguide 220. For example, the optical fiber 1160 may be lowered into a dicing lane or a trench, e.g., an etched trench or a deep silicon trench, on the wafer. The input end of the optical fiber 1160 is configured to couple the transmitted portion of the test light from the facet 230 into the optical fiber 1160 when the optical fiber 1160 is disposed substantially perpendicular to the chip plane. For example, the input end of the optical fiber 1160 may include an optical sub-assembly 1161, e.g., a prism, as shown in FIG. 11, an angled tip 1261, as shown in FIG. 12, or a bent end 1361, as shown in FIG. 13.

Figure 14:
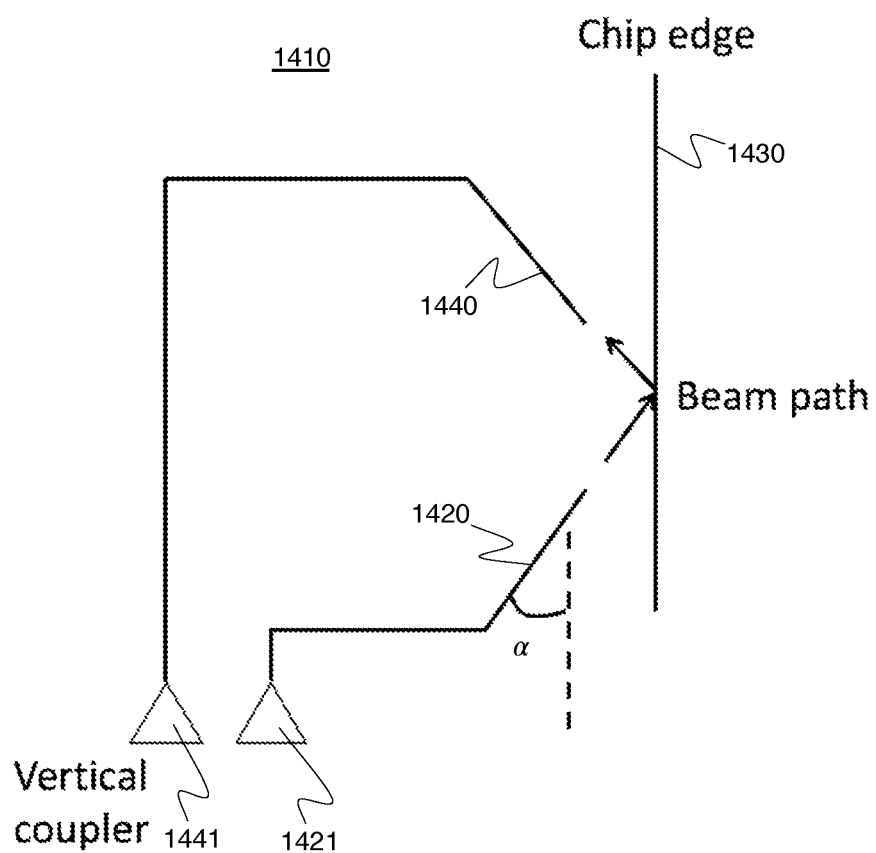
FIG. 14 is a schematic illustration of a top view of a test structure.
Figure 15:
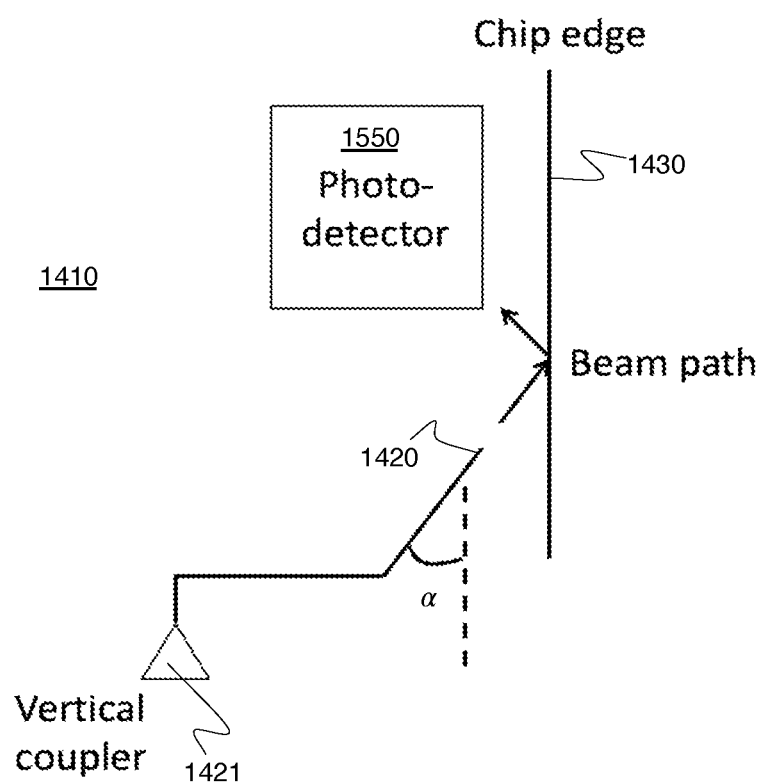
FIG. 15 is a schematic illustration of a top view of a test structure.
Figure 16:
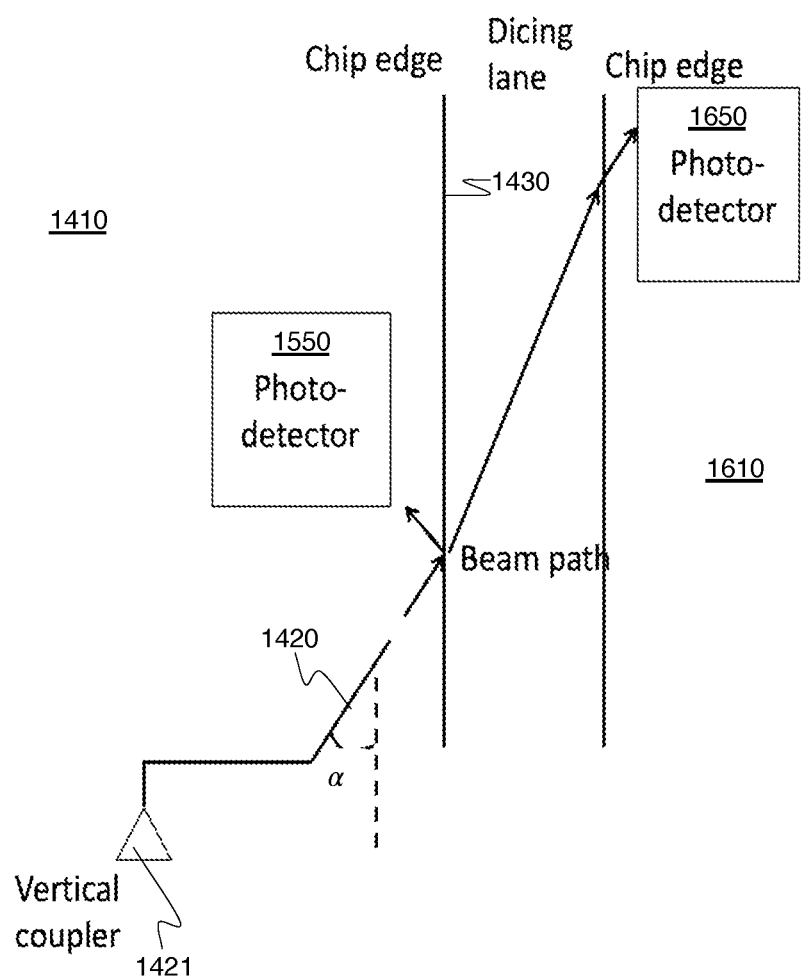
FIG. 16 is a schematic illustration of a top view of a test structure.
Figure 17:
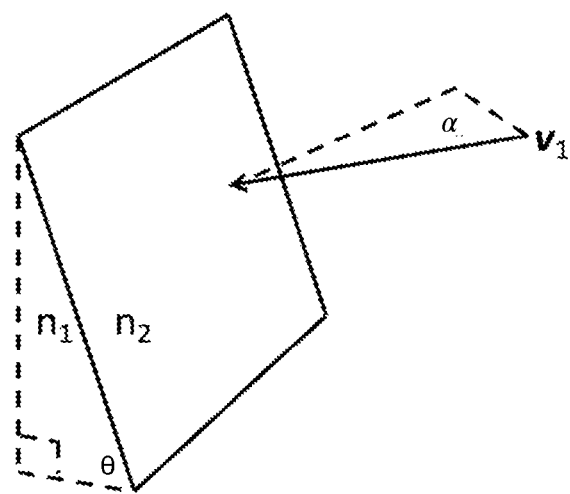
FIG. 17 is a schematic illustration of a relationship between waveguide angle, facet angle, and critical angle.

In the exemplary embodiments of FIGS. 14, 15, and 16, the test structure comprises a first chip 1410, typically a photonic chip, that includes a first waveguide 1420 configured to direct test light towards the facet 1430 in a direction at an oblique first angle $\alpha$ to the top edge of the facet 1430. At least an output segment of the first waveguide 1420 is disposed at the first angle to the top edge of the facet 1430. When the test light is incident on the facet 1430, a portion of the test light is reflected by the facet 1430. Depending on the first angle of the first waveguide 1420 and the facet angle, the test light may be substantially totally internally reflected by the facet 1430. If the test light is not substantially totally internally reflected, a portion of the test light is transmitted by the facet 1430. As shown in FIG. 17, the incidence angle $\phi$ of the test light, defined relative to the facet normal, depends on both the first angle $\alpha$ and the facet angle $\theta$ according to $\phi=\sqrt{\alpha^2+\theta^2}$, and total internal reflection occurs for the critical incidence angle $\phi_c$ when $$\phi_c = \arcsin\left(\frac{n_2}{n_1}\right),$$

where $n_1$ and $n_2$ are the refractive indices bounding the facet 1430. Accordingly, the first angle of the first waveguide 1420 may be selected such that total internal reflection is sensitive to the facet angle.

The test structure may be included in a test system that also includes a light source, a detector, and/or a processor. The light source, e.g., a laser or a broadband light source, is configured to provide the test light. The detector, e.g., a photodetector, is configured to measure an amount, e.g., an optical power, of the reflected portion of the test light or the transmitted portion of the test light. Typically, the detector detects the reflected portion of the test light or the transmitted portion of the test light and provides an output signal representative of the amount of the reflected portion of the test light or the transmitted portion of the test light to the processor. The processor, e.g., a general-purpose processor or a special-purpose processor, is configured, e.g., programmed with instructions, to determine a surface characteristic of the facet 1430, such as a facet angle, a facet curvature, and/or a facet roughness, on the basis of the measured amount.

Typically, the measured amount is compared to a threshold amount to determine whether the surface characteristic, typically the facet angle, is within a range corresponding to total internal reflection. For example, if a measured optical power of the reflected portion of the test light is greater than a threshold optical power, then the facet angle is determined to be within a facet-angle range providing total internal reflection. For another example, if a measured optical power of the transmitted portion of the test light is greater than a threshold optical power, then the facet angle is determined to be outside of a facet-angle range providing total internal reflection. In some instances, a plurality of first waveguides 1420, each having output segments disposed at different first angles relative to the top edge of the facet 1430, may be used to determine the surface characteristic, typically the facet angle, more precisely. By determining which of the first angles result in the test light being substantially totally internally reflected by the facet 1430, both a lower bound and an upper bound for the facet angle may be determined.

In the embodiment of FIG. 14, the first photonic chip 1410 further includes a first vertical coupler 1421, e.g., a grating coupler, as an input port, a second waveguide 1440, and a second vertical coupler 1441, e.g., a grating coupler, as an output port. The first vertical coupler 1421 is configured to couple the test light from an off-chip light source into the first waveguide 1420. The second waveguide 1440 is disposed at a substantially same height as the first waveguide 1420 in a reflection path of the reflected portion of the test light, and is configured to receive the reflected portion of the test light from the facet 1430. At least an input segment of the second waveguide 1440 is disposed at a second angle to the top edge of the facet 1430, the second angle being substantially equal in magnitude to the first angle. The second vertical coupler 1441 is configured to couple the reflected portion of the test light from the second waveguide 1440 to an off-chip detector configured to measure the amount of the reflected portion of the test light.

The embodiment of FIG. 15 is similar to the embodiment of FIG. 14, but the first photonic chip 1410 includes a first integrated photodetector 1550, e.g., a large-area photodetector, in place of the second waveguide 1440 and the second vertical coupler 1441. The first integrated photodetector 1550 is disposed near the facet 1430 at a substantially same height as the first waveguide 1420 in a reflection path of the reflected portion of the test light, and is configured to receive the reflected portion of the test light from the facet 1430 and to measure the amount of the reflected portion of the test light.

The embodiment of FIG. 16 is similar to the embodiment of FIG. 15, but further includes a second chip 1610, typically a photonic chip, including a second integrated photodetector 1650. The second photonic chip 1610 is disposed across a dicing lane from the first photonic chip 1410 on the same wafer as the first photonic chip 1410. The second integrated photodetector 1650 is disposed on the second photonic chip 1610 in a transmission path of the transmitted portion of the test light, and is configured to receive the transmitted portion of the test light and to measure the amount of the transmitted portion of the test light.

Figure 18:
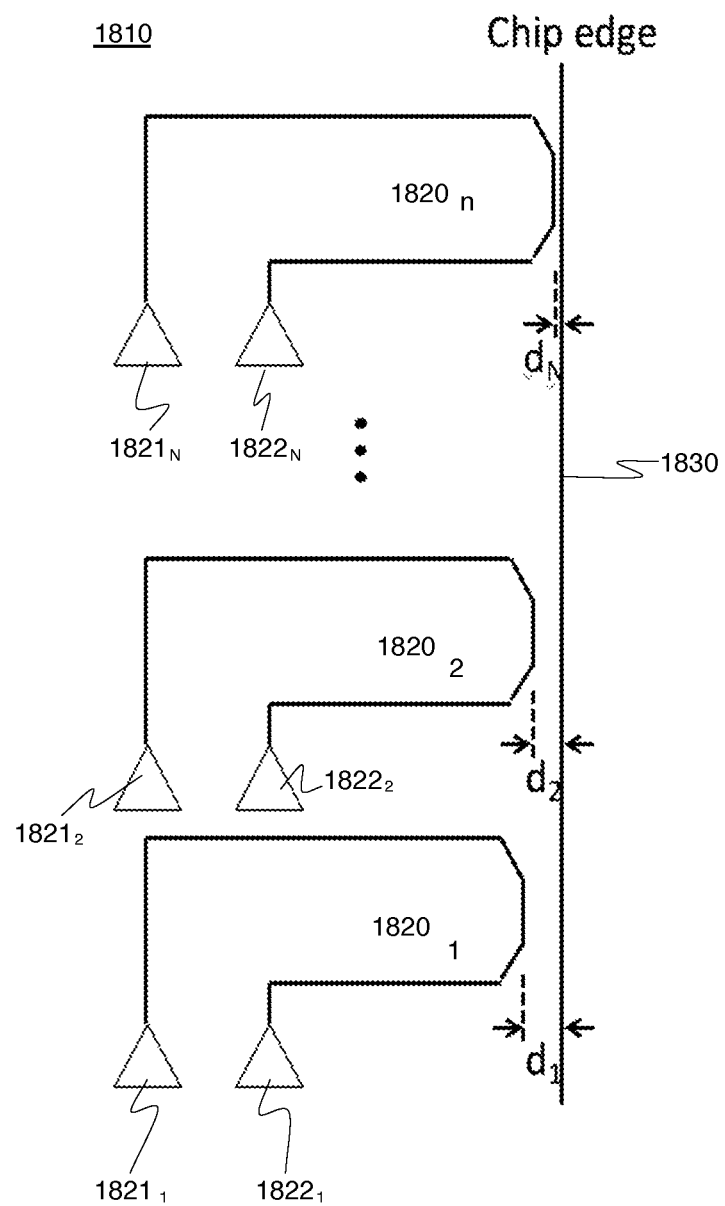
FIG. 18 is a schematic illustration of a top view of a test structure.
Figure 19:
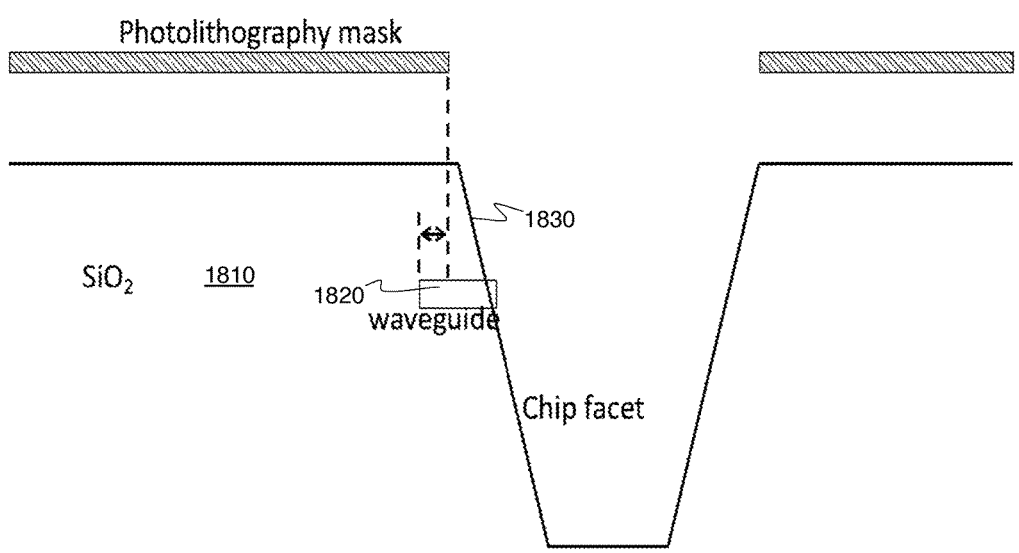
FIG. 19 is a schematic illustration of a cross-sectional side view of a test structure.
Figure 20:
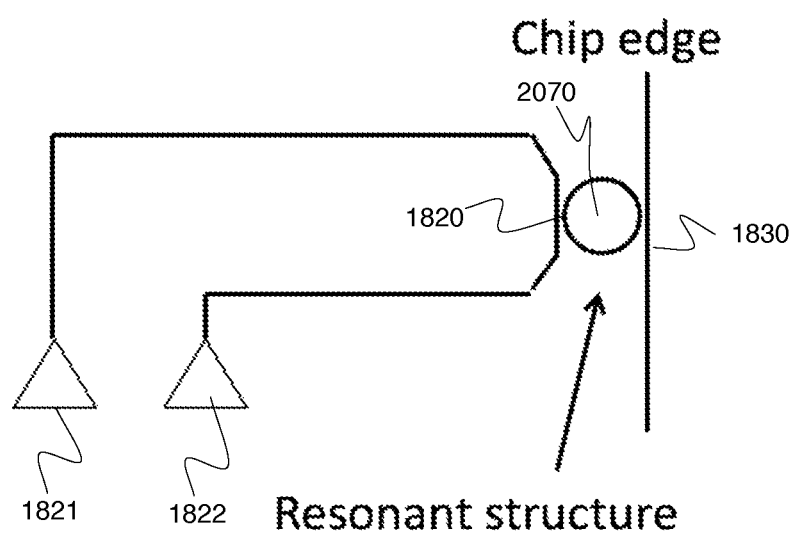
FIG. 20 is a schematic illustration of a top view of a test structure.

In the exemplary embodiments of FIGS. 18 to 20, the test structure comprises a chip 1810, typically a photonic chip, that includes one or more waveguides 1820 configured to direct test light in a direction substantially parallel to a top edge of a facet 1830 of the photonic chip 1810. At least a test segment of each waveguide 1820 is disposed substantially parallel to the top edge of the facet 1830.

The test structure may be included in a test system that also includes a light source, a detector, and/or a processor. The light source, e.g., a laser or a broadband light source, is configured to provide the test light. The detector, e.g., a photodetector, is configured to measure an amount, e.g., an optical power, of the test light transmitted by the waveguide 1820. Typically, the detector detects the transmitted test light and provides an output signal representative of the amount of the transmitted test light to the processor. The processor, e.g., a general-purpose processor or a special-purpose processor, is configured, e.g., programmed with instructions, to determine a surface characteristic of the facet 1830, such as a facet angle, a facet curvature, and/or a facet roughness, on the basis of the measured amount.

In the embodiment of FIG. 18, the photonic chip 1810 includes a plurality of input vertical couplers 1821, e.g., grating couplers, as input ports, a plurality of waveguides 1820, and a plurality of output vertical couplers 1822, e.g., grating couplers, as output ports. Each of the plurality of waveguides 1820 includes a test segment disposed at a substantially same height and substantially parallel to the top edge of the facet 1830 at a different distance from the facet 1830. Each of the plurality of input vertical couplers 1821 is configured to couple the test light from an off-chip light source into a waveguide 1820, and each of the plurality of second vertical couplers 1822 is configured to couple the test light from the waveguide 1820 to an off-chip detector configured to measure the amount of the test light transmitted by the waveguide 1820.

Prior to forming the facet 1830, the test segments are formed near the expected location of the facet 1830, typically so as to bound the expected location. When the facet 1830 is formed, e.g., by etching, some of the test segments may be entirely or partially removed. For example, as shown in FIG. 19, depending on the location of the photolithography mask relative to a test segment 1820, the test segment 1820 may be etched or the propagating electric field may extend beyond the facet 1830. Any of the plurality of waveguides 1820 including a test segment that is entirely or partially removed will no longer effectively transmit the test light between the input and output ports. By determining which of the plurality of waveguides 1820 transmit light and which do not, the location of the facet 1830 relative to the waveguide locations can be determined. Since each waveguide location and the facet location at the surface of the photonic chip 1810, e.g., the etch start location, are predetermined, e.g., lithographically defined, the facet angle from chip surface to the waveguide location can be determined. The processor may be configured to determine the facet angle on the basis of the measured amounts of test light transmitted by each waveguide 1820 and the predetermined waveguide locations.

The embodiment of FIG. 20 is similar to the embodiment of FIG. 18, but the photonic chip 1810 further includes at least one resonator 2070, e.g., a ring resonator, coupled to at least one waveguide 1820, e.g., by a directional coupler. The resonator 2070 is disposed adjacent to the test segment of the waveguide 1820, between the test segment and the facet 1830. A portion of the test light is coupled from the waveguide 1820 into the resonator 2070 and back into the waveguide 1820. Accordingly, a detector may be configured to measure the amount of test light transmitted by the waveguide 1820 as a function of spectral position, i.e., frequency or wavelength, in order to obtain a transmission spectrum of the resonator 2070. As the transmission spectrum of the resonator 2070 may depend on the proximity of the resonator 2070 to the facet 1830 and/or on a surface characteristic of the facet 1830, the processor may be configured to determine the surface characteristic of the facet 1830 on the basis of the transmission spectrum. For example, proximity to the facet 1830 and/or facet roughness may increase optical loss in the resonator 2070 and reduce the quality (Q)-factor of the resonator 2070, altering the transmission spectrum of the resonator 2070.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Further, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes.

We claim:

1. A test system for determining a surface characteristic of a chip facet, the test system comprising:
    a first chip having a facet, the first chip including a first waveguide configured to direct test light towards the facet;
    a detector configured to measure an amount of a portion of the test light reflected by the facet or a portion of the test light transmitted by the facet; and
    a processor configured to determine a surface characteristic of the facet on the basis of the measured amount;
    wherein the first waveguide is configured to receive the reflected portion of the test light from the facet, wherein the first chip further includes a second waveguide, wherein the first waveguide and the second waveguide are coupled by a directional coupler or a multimode interference coupler, and wherein the detector is coupled to the second waveguide to measure the reflected portion of the test light.

2. The test system of claim 1, wherein the first chip is disposed in a wafer.

3. The test system of claim 1, wherein the surface characteristic is one of: a facet angle, a facet curvature, or a facet roughness.

4. The test system of claim 1, wherein the first waveguide is configured to direct the test light towards the facet in a direction perpendicular to a top edge of the facet.

5. The test system of claim 1, wherein the facet includes a lithographically defined feature near the first waveguide, and wherein the lithographically defined feature is configured to facilitate reflection of the reflected portion of the test light or to facilitate transmission of the transmitted portion of the test light.

6. The test system of claim 1, wherein the first waveguide is disposed at a different height from a main face of the first chip than the second waveguide.

7. The test system of claim 1, wherein the first waveguide forms a test arm of a Michelson interferometer, and wherein the second waveguide forms a reference arm of the Michelson interferometer.

8. The test system of claim 7, wherein the first chip further includes a phase shifter and a mirror, wherein the second waveguide is configured to direct reference light towards the mirror, and wherein the phase shifter is configured to phase shift the reference light.

9. The test system of claim 7, wherein the reference arm has an adjustable optical path length.

10. The test system of claim 9, wherein the optical path length is thermally adjustable or is adjustable by adjusting a charge-carrier concentration in the reference arm.

11. The test system of claim 7, wherein the detector is a balanced photodetector configured to measure the amount of the reflected portion of the test light as an interference pattern.

12. The test system of claim 4, wherein the detector is an integrated photodetector included in the first chip.

13. The test system of claim 1, wherein the facet is inclined, and wherein the first waveguide includes a grating structure configured to diffract the test light such that the test light is directed towards the facet in a direction substantially perpendicular to the inclined facet.

14. The test system of claim 1 wherein the facet is defined at an edge of the first chip or as a sidewall of a trench.

15. A test system for determining a surface characteristic of a chip facet, the test system comprising:
    a first chip comprising:
        a facet, and
        a first waveguide configured to direct test light towards the facet at an oblique first angle to a top edge of the facet;
    a second chip disposed across a dicing lane from the first chip on a same wafer as the first chip;
    a detector configured to measure a transmitted portion of the test light transmitted by the facet; and
    a processor configured to determine a surface characteristic of the facet on the basis of the transmitted portion;
    wherein the detector is an integrated photodetector included in the second chip, wherein the detector is configured to receive the transmitted portion of the test light and to measure the amount of the transmitted portion of the test light.

16. A test system for determining a surface characteristic of a chip facet, the test system comprising:
    a first chip comprising a facet and a first waveguide configured to direct test light towards the facet;
    a detector configured to measure a reflected portion of the test light reflected by the facet;
    a processor configured to determine a surface characteristic of the facet on the basis of the reflected portion measured by the detector; and
    wherein the first chip further comprises a second waveguide configured to receive the reflected portion of the test light from the facet, wherein the first waveguide is configured to direct the test light towards the facet at an oblique first angle to a top edge of the facet, and wherein the detector is configured to measure the reflected portion of the test light received from the second waveguide; and,
    wherein the first waveguide includes an output segment disposed at the first angle to the top edge, wherein the second waveguide includes an input segment disposed at a second angle to the top edge, and wherein the first angle and the second angle are substantially equal in magnitude.

* * * * *